(12) United States Patent
Woltering et al.

(10) Patent No.: US 7,429,676 B2
(45) Date of Patent: Sep. 30, 2008

(54) PROCESS FOR PREPARING ENANTIOMERICALLY ENRICHED 2-ALKOXY-3-PHENYLPROPIONIC ACIDS

(75) Inventors: Michael Woltering, Hilden (DE); Tanasri Bunlaksananusorn, Creil (FR); Arne Gerlach, Sulzbach (DE)

(73) Assignee: Saltigo GmbH, Leverkusen (DE)

( * ) Notice: Subject to any disclaimer, the term of this patent is extended or adjusted under 35 U.S.C. 154(b) by 0 days.

(21) Appl. No.: 11/635,302

(22) Filed: Dec. 7, 2006

(65) Prior Publication Data

US 2007/0149804 A1 Jun. 28, 2007

(30) Foreign Application Priority Data

Dec. 22, 2005 (DE) ........................ 10 2005 061 472

(51) Int. Cl.
*C07C 63/00* (2006.01)
*C07C 59/00* (2006.01)
*C07C 65/00* (2006.01)

(52) U.S. Cl. ...................... 562/405; 562/465; 562/470
(58) Field of Classification Search ................ 562/405, 562/465, 470
See application file for complete search history.

(56) References Cited

U.S. PATENT DOCUMENTS

| | | | | | |
|---|---|---|---|---|---|
| 3,030,359 | A | * | 4/1962 | Arens et al. ................. | 540/38 |
| 4,239,914 | A | * | 12/1980 | Campolmi et al. .......... | 562/466 |
| 5,233,084 | A | * | 8/1993 | Chan ........................... | 562/466 |
| 2007/0142472 | A1 | | 6/2007 | Yokozawa et al. | |

FOREIGN PATENT DOCUMENTS

| | | |
|---|---|---|
| JP | 2001 261612 | 9/2001 |
| WO | WO 00/26200 | 5/2000 |
| WO | WO 01/11072 | 2/2001 |
| WO | 2005/051882 | 6/2005 |
| WO | WO 2005/051882 | 6/2005 |

OTHER PUBLICATIONS

Linderberg et al. Organic Process Research & Development, 2004, vol. 8, pp. 838-845.*
Nitta et al. Journal of Molecular Catalysis A: Chemical 212, 2004, pp. 155-159.*
Yuriko Nitta. Bulletin of the Chemical Society of Japan, 2001, vol. 74, pp. 1971-1972.*
Jones et al. Topics in Catalysis, 2003, vol. 25 (1-4), pp. 71-79.*
Nitta et al. Bulletin of the Chemical Society of Japan, 2001, vol. 74, pp. 2161-2165.*
Rouzaud et al. Helvetica Chimica Acta, 2003, vol. 86, pp. 1753-1759.*
Burk et al. Journal of the American Chemical Society, 1998, vol. 10, pp. 4345-4353.*
Lohray et al. Journal of Medicinal Chemistry, 2001, vol. 44, pp. 2675-2678.*
Schmidt, Ulrich, et al.; "Synthesis and Enantioselective Hydrogenation of α-Acyloxyacrylates," *Synthesis*, Nov. 1994, pp. 1138-1140.
Burk, Mark J., et al.; "Rh-DuPHOS-Catalyzed Enantioselective Hydrogenation of Enol Esters. Application to the Synthesis of Highly Enantioenriched α-Hydroxy Esters and 1,2-Diols," *J. Am. Chem. Soc.*, 1998, 120, pp. 4345-4353.
Lohray, Braj B., et al.; "(−)-3-[4-[2-(Phenoxazin-10yl)ethoxy]phenyl]-2-ethoxypropanoic Acid [(−)DRF 2725]: A Dual PPAR Agonist with Potent Antihyperglycemic and Lipid Modulating Activity," *J. Med. Chem.* 2001, 44, pp. 2675-2678.
Deussen, Heinz-Josef, et al.; "Process Development on the Enantioselective Enzymatic Hydrolysis of S-Ethyl 2-Ethoxy-3-(4-hydroxyphenyl)propanoate," *Organic Process Research & Development*, 2003, 7, pp. 82-88.
Tang, Wenjun, et al.; "New Chiral Phosphorus Ligands for Anantioselective Hydrogenation;" *Chem. Rev.* 2003, 103, pp. 3029-2069.
Linderberg, Mats T.; "Claisen Condensation as a Facile Route to an α-Alkoxy-cinnamate: Synthesis of Ethyl (2S)-2-Ethoxy-3-(4-hydroxyphenyl)propanoate," *Organic Process Research & Development*, 2004, 8, pp. 838-845.
P. E. Maligres et al., "Enantioselective Hydrogenation of α-Aryloxy α,β-Unsaturated Acids. Asymmetric Synthesis of α-Aryloxycarboxylic Acids", Organic Letters, vol. 6, No. 18, pp. 3147-3150, 2004.

* cited by examiner

*Primary Examiner*—Sikarl A Witherspoon
(74) *Attorney, Agent, or Firm*—Michael A. Miller

(57) ABSTRACT

The present invention relates to a process for preparing enantiomerically enriched, optionally substituted 2-alkoxy-3-phenylpropionic acids by asymmetrically hydrogenating alkoxy-cinnamic acids.

18 Claims, No Drawings

PROCESS FOR PREPARING ENANTIOMERICALLY ENRICHED 2-ALKOXY-3-PHENYLPROPIONIC ACIDS

The present invention relates to a process for preparing enantiomerically enriched, optionally substituted 2-alkoxy-3-phenylpropionic acids by asymmetrically hydrogenating 2-alkoxycinnamic acids.

Substituted 2-alkoxy-3-phenylpropionic acids constitute an interesting class of active ingredients which have gained increasing significance in the last few years as a structural motif especially in agonists of peroxisome proliferator-activated receptors (PPARs). Agonists of these receptors find use predominantly in substances for the treatment of diabetes and disorders of lipid metabolism (e.g. ragaglitazar, tesaglitazar, NNC 61-4655, inter alia). Accordingly, the provision of highly enantiomerically pure 2-alkoxy-3-phenylpropionic acid units is of particular interest for the preparation of such active substances.

For the preparation of substituted 2-alkoxy-3-phenylpropionic acids, various processes have been described in terms of concept.

J. Med. Chem. 2001, 44, 2675-2679 describes a chromatographic diastereomer separation of the particular amides, which have been formed from the racemic acid with addition of chiral enantiomerically pure amines.

In addition, the possibility exists of optical resolution by means of diastereomer crystallization. For instance, WO-A 2004/00789 describes the optical resolution of the racemic substituted 2-alkoxy-3-phenylpropionic acids with chiral bases by diastereomer crystallization and WO-A 2000/26200 the resolution of the racemic substituted 2-alkoxy-3-phenylpropionic acids. Such diastereomer crystallizations can also follow a chiral pool synthesis (cf. WO-A 2000/26200, WO-A 2002/26425).

Kinetic optical resolutions of racemic substituted 2-alkoxy-3-phenylpropionic acids by enzymatic processes such as ester hydrolysis, esterification or transesterification have also been described in the literature (cf. WO-A 2001/11072 and WO-A 2001/11073). Org. Proc. Res. & Dev. 2003, 82 describes, for example, the preparation of (S)-3-(4-hydroxyphenyl)-2-ethoxypropionic acid based on enzymatic ester hydrolysis in detail.

What is common to the above processes is that the actual synthesis of the 2-alkoxy-3-phenylpropionic acids must be followed by the optical resolution in a separate step. For economic optimization of such syntheses among other reasons, there is therefore a general search for alternatives which include the enantioselective synthetic steps actually in the formation of the molecule.

Such a synthesis is described, for example, in WO-A 2002/100813 with an enantioselective reduction of 2-oxo-3-phenylpropionic acid with (+)-chlorodiisopinocampheylborane to give the 2-hydroxy acid which can in turn then be converted to the 2-alkoxy ester and then to the 2-alkoxy acid. For the enantioselective hydrogenation on substituted cinnamic acids, examples of 2-acylaminocinnamic esters have also been described (Chem. Rev. 2003, 3029); in addition, examples of the hydrogenation of 2-acyloxycinnamic esters and benzylidenesuccinic esters are also known (J. Am. Chem. 1998, 4345; Synthesis 1994, 1138; Synlett 2002, 837).

However, these processes have the disadvantage that, firstly owing to the protecting group technique used, a series of process steps for selective introduction and elimination of the appropriate protecting groups have to be passed through, and, secondly, all of these processes go through the corresponding propionic esters which have to be converted to the corresponding propionic acids in a further step.

There is thus still a need for a process for preparing enantiomerically enriched 2-alkoxy-3-phenylpropionic acids which leads to the desired products with high enantiomeric excess with fewer process steps.

The object underlying the present invention is thus that of discovering such a process for preparing enantiomerically enriched 2-alkoxy-3-phenylpropionic acids.

It has now been found that, surprisingly, enantiomerically enriched 2-alkoxy-3-phenylpropionic acids can be prepared by asyimetrically hydrogenating alkoxycinnamic acids in a simple process without a protecting group technique with a high enantiomeric excess using a transition metal hydrogenation catalyst.

The present invention provides a process for preparing enantiomerically enriched compounds of the general formula (I)

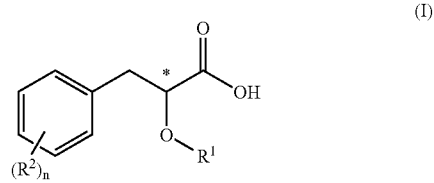

where
$R^1$ is an optionally substituted $C_1$-$C_{18}$-alkyl radical, preferably a $C_1$-$C_6$-alkyl radical, an optionally substituted $C_4$-$C_{24}$-aryl radical, preferably a $C_6$-$C_{24}$-alkyl radical, or an optionally substituted $C_5$-$C_{18}$-arylalkyl radical, $R^2$ are each independently OH, halogen, pseudohalogen, amino, an optionally substituted $C_1$-$C_{18}$-alkyl radical, preferably a $C_1$-$C_6$-alkyl radical, an optionally substituted $C_1$-$C_{18}$-alkoxy radical, preferably a $C_1$-$C_6$-alkoxy radical, an optionally substituted $C_4$-$C_{24}$-aryl radical, preferably a $C_6$-$C_{24}$-aryl radical, an optionally substituted $C_5$-$C_{18}$-arylalkyl radical, an optionally substituted $C_1$-$C_{18}$-alkylsulphonyl radical, an optionally substituted $C_1$-$C_{18}$-alkylcarboxyl radical, an optionally substituted $C_1$-$C_{18}$-alkylcarbonyl radical, an optionally substituted $C_1$-$C_{18}$-mono- or dialkylamino radical, preferably a $C_1$-$C_6$-mono- or dialkylamino radical, an optionally substituted $C_1$-$C_{18}$-alkylsulphonylamino radical or an optionally substituted $C_1$-$C_{18}$-acylamino radical. Preference is given here to OH, halogen, a $C_1$-$C_6$-alkyl radical, a $C_1$-$C_6$-alkoxy radical or a $C_5$-$C_{18}$-arylalkyl radical; particular preference is given to OH.

n is 0 or an integer from 1 to 5, preferably 1, 2 or 3, more preferably 1, wherein compounds of the general formula (II)

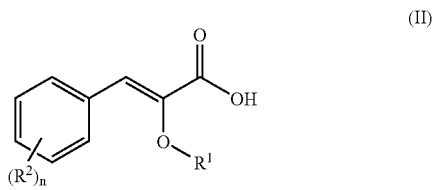

where
R¹, R² and n are each as defined for the general formula (I) are hydrogenated enantioselectively in the presence of a transition metal hydrogenation catalyst.

In a preferred embodiment of the process according to the invention, the compounds of the general formula (II) are prepared from compounds of the general formula (III)

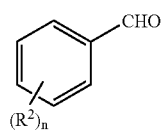

where
R² and n are each as defined for the general formula (I),
and compounds of the general formula (IV)

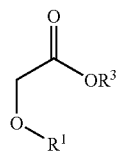

where
R³ is H or an optionally substituted $C_1$-$C_{18}$-alkyl radical, preferably a $C_1$-$C_6$-alkyl radical, and
R¹ is as defined for the general formula (I), in an aldol reaction in the presence of a base, and subsequent hydrolysis if appropriate.

The carbon atom indicated with * in the general formula (I) is an asymmetric carbon atom. Enantiomerically enriched compound of the general formula (I) in the context of the invention means the enantiomerically pure compounds of the general formula (I) in (R) or (S) configuration, or mixtures of the particular two enantiomers in which one enantiomer is present in an enantiomeric excess, also referred to hereinafter as ee ("enantiomeric excess"), in comparison to the other enantiomer. This enantiomeric excess is preferably 2 to 100% ee, more preferably 60% to 100% ee and most preferably 85 to 100% ee. A definition of the ee value is given in the examples of this application.

In the context of the invention, all radical definitions, parameters and illustrations above and listed below, in general or within areas of preference, may be combined with one another in any manner, i.e. including between the particular areas and areas of preference.

Alkyl or alkoxy means in each case a linear, cyclic, branched or unbranched alkyl or alkoxy radical. The same applies to the nonaromatic moiety of an arylalkyl radical or to the alkyl moiety of an alkylsulphonyl, alkylcarboxyl, alkylcarbonyl, mono- or dialkylamino, and alkylsulphonylamino radical.

$C_1$-$C_6$-Alkyl is, for example, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl; $C_1$-$C_{18}$-alkyl is additionally, for example, n-heptyl and n-octyl, pinacolyl, adamantyl, the isomeric menthyls, n-nonyl, n-decyl, n-dodecyl, n-tridecyl, n-tetradecyl, n-hexadecyl or n-octadecyl.

$C_1$-$C_6$-Alkoxy is, for example, the alkoxy groups corresponding to the above alkyl groups, for example methoxy, ethoxy, n-propoxy, isopropoxy, n-butoxy, sec-butoxy, tert-butoxy, n-pentoxy, n-hexoxy, etc. $C_1$-$C_{18}$-Alkoxy is, for example, the alkoxy groups corresponding to the above alkyl groups.

$C_1$-$C_{18}$-Alkylsulphonyl, $C_1$-$C_{18}$-alkylcarboxyl, $C_1$-$C_{18}$-alkylcarbonyl, $C_1$-$C_6$-mono- or dialkylamino or $C_1$-$C_{18}$-mono- or dialkylamino or $C_1$-$C_{18}$-alkylsulphonylamino is, for example, the alkylsulphonyl, alkylcarboxyl, alkylcarbonyl, mono- or dialkylamino or alkylsulphonylamino groups corresponding to the above alkyl groups.

Aryl is in each case independently an aromatic radical having from 4 to 24 skeleton carbon atoms, in which no, one, two or three skeleton carbon atoms per cycle but at least one skeleton carbon atom in the entire molecule may be substituted by heteroatoms selected from the group of nitrogen, sulphur and oxygen, but is preferably a carbocyclic aromatic radical having 6 to 24 skeleton carbon atoms. The same also applies to the aryl moiety of an arylcarbonyl radical.

Examples of $C_6$-$C_{24}$-aryl are phenyl, o-, p-, m-tolyl, naphthyl, phenanthrenyl, anthracenyl or fluorenyl. Examples of heteroaromatic $C_4$-$C_{24}$-aryl in which no, one, two or three skeleton carbon atoms per cycle but at least one skeleton carbon atom in the entire molecule may be substituted by heteroatoms selected from the group of nitrogen, sulphur or oxygen are, for example, pyridinyl, oxazolyl, benzofuranyl, dibenzofuranyl or quinolinyl.

Arylalkyl is in each case independently a straight-chain, cyclic, branched or unbranched alkyl radical as defined above, which may be substituted singly, multiply or fully by aryl radicals as defined above.

$C_5$-$C_{18}$-Arylalkyl is, for example, benzyl or (R)- or (S)-1-phenylethyl.

Halogen may be fluorine, chlorine, bromine or iodine. Pseudohalogen may, for example, be cyanide, cyanate or thiocyanate.

Possible substituents for the R¹, R² or R³ radicals include numerous organic groups, for example alkyl, cycloalkyl, aryl, halogen, hydroxyl, ether, thioether, disulphide, sulphoxide, sulphonic acid, sulphonate, amino, aldehyde, keto, carboxylic ester, carbonate, carboxylate, cyano, alkylsilane and alkoxysilane groups, and also carboxamide groups.

R¹ is preferably an optionally substituted $C_1$-$C_6$-alkyl radical, and in a preferred embodiment of the process according to the invention is methyl.

R² is preferably independently OH, F, Cl, Br, CN, an optionally substituted $C_1$-$C_6$-alkyl radical, an optionally substituted $C_6$-$C_{24}$-aryl radical or an optionally substituted $C_5$-$C_{18}$-arylalkyl radical, and in a preferred embodiment of the process according to the invention is OH.

R³ is preferably H or an optionally substituted $C_1$-$C_6$-alkyl radical, and in a preferred embodiment of the process according to the invention is methyl.

R² in the general formula (III) may be in ortho, meta or para position to the aldehyde group and hence, in the compounds of the general formulae (I) and (II), likewise in the corresponding position to the propionyl substituent. In preferred embodiments, R² is in the para position.

Preferably in accordance with the invention, the transition metal hydrogenation catalyst used is a catalyst system comprising at least one transition metal compound, for example ruthenium, rhodium, iridium, rhenium, cobalt or chromium compound, and at least one ligand. Particular preference is given to a catalyst system comprising at least one ruthenium, rhodium or iridium compound and at least one ligand.

The individual components—i.e. transition metal compound(s) and ligand(s)—of the catalyst system are preferably soluble in the solvent used if appropriate, soluble in the context of the invention meaning that at least a portion of the individual components of the catalyst system is soluble in the solvent used. Full solubility is not absolutely necessary.

Preferred ruthenium, rhodium or iridium compounds are Ru(II) compounds, Rh(I) compounds and Ir(I) compounds. For example, the ruthenium, rhodium or iridium compounds used are $[RuCl_2(p\text{-cymene})]_2$, $Ru(COD)Cl_2$, $[Ru(C_6H_6)Cl_2]_2$, $Rh(COD)_2BF_4$, $[Rh(COD)Cl]_2$, $Rh(NBD)_2BF_4$, $[Rh(NBD)Cl]_2$, $Ir(COD)_2BF_4$ or $[Ir(COD)Cl]_2$, where COD is 1,5-cyclooctadienyl and NBD is norbonadienyl.

Preferred possible ligands are chiral ligands. Especially useful are chiral phosphine ligands. Particular preference is given to chiral diphosphine ligands, for example (S,S)-2,4-bis(diphenylphosphinyl)pentane, (−)-2,2'-dichloro-3,3'-dimethoxy-6,6'-bis-(diphenylphosphinyl)biphenyl, (−)-3,3'-bis(diphenylphosphinyl)-[4,4']bi(dibenzofuranyl), or their enantiomers.

In the context of the invention, the transition metal hydrogenation catalyst may be used either as an isolated complex or be generated in situ. The transition metal hydrogenation catalyst is preferably generated in situ. In the latter case, one or more suitable transition metal compound(s) and the ligand(s) are combined in a suitable solvent, optionally in an inert gas atmosphere, and the mixture is optionally then heated.

Transition metal compound(s) and ligand(s) are present in the catalyst system, depending on the transition metal compound, for example, in a quantitative ratio of 1:0.8 to 1:4 (transition metal compound(s) to ligand(s)). For chiral diphosphine ligands, preference is given to ratios of 1:0.9 to 1:2.5.

In the context of the invention, the amount of the transition metal hydrogenation catalyst used is, for example, between 0.001 and 20 mol %, preferably between 0.01 and 10 mol % and more preferably between 0.1 and 5 mol %, based on the amount of the compound of the general formula (II).

Preference is given to performing the enantioselective hydrogenation in the presence of at least one protic solvent. Suitable protic solvents include, for example, alcohols, for example methanol, ethanol, n-propanol, isopropyl alcohol, n-butanol, sec-butanol, tert-butanol, tert-amyl alcohol, sec-amyl alcohol. These may be used alone or in combination with other suitable solvents. Other suitable solvents include carboxylic esters, for example ethyl acetate, isopropyl acetate, n-propyl acetate, n-butyl acetate, halogenated aliphatic hydrocarbons, for example dichloromethane, 1,2-dichloroethane, chloroform, tetrachloromethane, cyclic or aliphatic ethers, for example tetrahydrofuran, dioxane, tert-butyl methyl ether, cyclic or aliphatic hydrocarbons, for example cyclohexane, pentane, hexane, heptane, aromatic hydrocarbons, for example toluene, xylene, cumene, cymene, or mixtures thereof or comprising one or more thereof.

Preference is given to performing the enantioselective hydrogenation at temperatures of 10 to 120° C., more preferably of 20 to 100° C., in preferred embodiments of 40 to 80° C. The reaction time is preferably several hours, more preferably 0.2 to 48 h, most preferably 10 to 30 h.

The performance of the enantioselective hydrogenation under protective gas atmosphere, for example nitrogen or argon atmosphere, may be advantageous but is not absolutely necessary.

Preference is further given to performing the enantioselective hydrogenation, depending on the transition metal hydrogenation catalyst used, at 1 to 200 bar of hydrogen pressure. For example, when a catalyst system comprising a rhodium compound is used, a lower hydrogen pressure of, for example, 1 to 50 bar may lead to the optimal conversion, whereas, for a catalyst system comprising an iridium compound, under some circumstances, a higher hydrogen pressure of, for example, 1 to 100 bar, and, for a catalyst system comprising a ruthenium compound, under some circumstances, a hydrogen pressure of 5 to 180 bar may be advantageous with regard to the reaction profile.

Optionally, basic additives such as tertiary amines or alkali metal $C_1$-$C_{18}$-alkoxides, for example triethylamine or sodium methoxide, may be added to the enantioselective hydrogenation. This addition is preferably effected in an amount of 0.5 to 2 equivalents, preferably in virtually equimolar amounts, based on the amount of cinnamic acid derivative used.

The base used in the aldol reaction may comprise, for example, alkali metal or alkaline earth metal $C_1$-$C_{18}$-alkoxides, for example sodium or potassium methoxide, sodium or potassium ethoxide, sodium n-, sec- or tert-butoxide, potassium n-, sec- or tert-butoxide, or optionally substituted alkali metal or alkaline earth metal $C_1$-$C_{18}$-amides, for example lithium diisopropylamide or hexamethyldisilazane. Particular preference is given to using sodium methoxide. The base is preferably used in excess. Particular preference is given to amounts of 2 to 6 equivalents, most preferably of 4 to 5 equivalents, based on the amount of the compound of the general formula (III).

The aldol reaction is preferably performed in the presence of at least one solvent. Useful solvents are, for example, alcohols, for example methanol, ethanol, n-propanol, isopropyl alcohol, n-butanol, sec-butanol, tert-butanol, tert-amyl alcohol, sec-amyl alcohol, cyclic or open-chain ethers, for example diethyl ether, tert-butyl methyl ether, tetrahydrofuran, methyltetrahydrofuran, dioxane or tetrahydropyran, aromatic hydrocarbons, for example toluene, xylene, cumene, cymene, aliphatic hydrocarbons, for example n-petane, n-hexane, n-heptane, isohexane, cyclic hydrocarbons, for example cyclopentane, cyclohexane, methylcyclohexane, or mixtures thereof or comprising one or more thereof. Particular preference is given to alcohols or mixtures comprising alcohols.

Preference is given to performing the aldol reaction at temperatures of 10 to 120° C., more preferably of 20 to 100° C., in preferred embodiments of 40 to 80° C. The reaction time is preferably several hours, more preferably 0.2 to 48 h, most preferably 1 to 24 h. The reaction solution is preferably stirred until the conversion of the compound of the general formula (III) is virtually complete.

The aldol reaction can be performed at standard, elevated or reduced pressure, for example in the range from 0.5 to 5 bar. In general, it is performed at standard pressure.

The performance of the aldol reaction under protective gas atmosphere, for example nitrogen or argon atmosphere, may be advantageous but is not absolutely necessary.

On completion of virtually full conversion of the compound of the general formula (III), when $R^3$ is different from H, for hydrolysis and preparation of the compound of the general formula (II), for example, water can be added to the reaction solution. The hydrolysis can, however, also be effected separately after preceding isolation of the corresponding ester of the compound of the general formula (II). However, preference is given to performing the hydrolysis directly in the reaction solution without isolating the ester. Preference is given to performing the hydrolysis at temperatures of 10 to 120° C., more preferably of 20 to 100° C., in preferred embodiments of 30 to 80° C. During the hydrolysis, it may be advantageous to distil off part of the solvent. Subsequently, the reaction solution, optionally after preceding cooling, preferably to room temperature, can be acidified to precipitate the compound of the general formula (II). To this end, preference is given to using mineral acids. Suitable mineral acids are known to those skilled in the art; preference is given to using concentrated aqueous hydrochloric acid. Optionally, the acidified reaction solution, to complete the precipitation, is stirred for a certain time, preferably between 15 minutes and 10 hours at room temperature, and the compound of the general formula (II) is then isolated. The isolation can be effected by customary methods known to those skilled in the art, for example filtration.

The compounds of the general formula (IV) are used in the aldol reaction preferably in an amount of 1 to 4 equivalents based on the amount of the compound of the general formula (III). Particular preference is given to using the compounds of the general formula (IV) in excess; in a preferred embodiment, 2 to 3 equivalents of the compounds of the general formula (IV) are used based on the amount of the compound of the general formula (III).

The compounds of the general formulae (III) and (IV) are generally commercially available or can be prepared from commercially available precursors by means of commonly known preparation processes. In a preferred embodiment, the compound of the general formula (III) used is 4-hydroxybenzaldehyde and the compound of the general formula (IV) used is methyl methoxyacetate.

The compounds of the general formula (I) can be isolated either in the form of the free acids or else in the form of salts of the general formula (V)

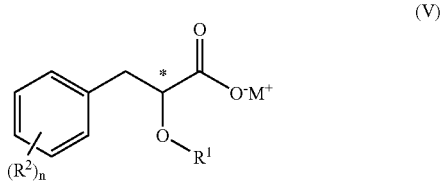

(V)

where $M^+$ is an alkali metal cation or ammonium, preferably $Na^+$, and $R^1$, $R^2$ and n are each as defined for the general formula (I).

The salts of the general formula (V) can be prepared after preceding intermediate isolation of the compounds of the general formula (I) or else without such a preceding intermediate isolation. If appropriate, a solvent change may be advantageous before the preparation of the salts of the general formula (V), which, however, should not be understood to be an intermediate isolation of the compounds of the general formula (I) in the context of the invention. To this end, the solvent used for the enantioselective hydrogenation is initially removed, optionally under reduced pressure, and the remaining residue is taken up in a further solvent without further purification steps. The further solvent may likewise comprise solvents which were also present in the solvent for the enantioselective hydrogenation.

Suitable further solvents for the preparation of the salts of the general formula (V) are, for example, alcohols, for example methanol, ethanol, n-propanol, isopropanol, n-butanol, carboxylic esters, for example ethyl acetate, isopropyl acetate, n-propyl acetate, n-butyl acetate, ketones, for example acetone, butyl methyl ketone, nitriles, for example acetonitrile, propionitrile, butyronitrile, cyclic or open-chain ethers, for example diethyl ether, dibutyl ether, tert-butyl methyl ether, tetrahydrofuran, dioxane, or solvents comprising one or more thereof. Preference is given here to carboxylic esters or solvent mixtures comprising them.

The salts of the general formula (V) are precipitated or crystallized out of the corresponding solution in the presence of an alkali metal or ammonium salt. Suitable alkali metal or ammonium salts include, for example, alkali metal or ammonium salts of carboxylic acids, for example acetates, preferably their sodium salts. Particular preference is given to using sodium acetate. Before they are added to the compounds of the general formula (I), the alkali metal or ammonium salts are dissolved or suspended fully or partly beforehand in a suitable solvent. Such suitable solvents are, for example, alcohols, for example methanol, ethanol, n-propanol, isopropyl alcohol, n-butanol, sec-butanol, tert-butanol, tert-amyl alcohol, sec-armyl alcohol, or carboxylic esters, for example ethyl acetate, isopropyl acetate, n-propyl acetate, n-butyl acetate, mixtures thereof or solvents comprising them.

The salts of the general formula (V) can be isolated by known processes, for example by filtration. Optionally, the enantiomeric purity of the salts of general formula (V) can be increased further by a subsequent recrystallization. Suitable solvents for such a recrystallization are, for example, alcohols, for example methanol, ethanol, n-propanol, isopropyl alcohol, n-butanol, sec-butanol, tert-butanol, tert-amyl alcohol, sec-amyl alcohol, or mixtures thereof or comprising one or more thereof.

The compounds of the general formula (I) prepared by the process according to the invention, if appropriate in the form of the corresponding salts of the general formula (V), are, as already mentioned at the outset, for example, active pharmaceutical ingredients which have gained increasing significance in the last few years as the structural motive, especially agonists of the peroxisome proliferator-activated receptors (PPARs). The process according to the invention affords, in comparison to known processes, a significantly simpler route to the enantiomerically enriched compounds of the general formula (I), since, firstly, the complicated protecting group technique is dispensed with and, secondly, the corresponding free propionic acids are obtained by a direct route. As a result, significantly fewer reaction steps are passed through in the process according to the invention than in known processes, although equally high enantiomeric excesses are achieved.

The examples which follow serve to illustrate the invention by way of example and are not to be interpreted as a restriction.

EXAMPLES

Example 1

Preparation of Z-4'-hydroxy-2-methoxycinnamic Acid

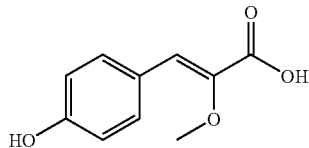

A solution of 150 g (1.20 mol) of 4-hydroxybenzaldehyde and 316 g (3.00 mol) of methyl methoxyacetate in 1.0181 (5.39 mol) of 30% sodium methoxide solution in methanol was heated under reflux for 6 h. Subsequently, the mixture was cooled to 40° C. and admixed with 1 l of water. 760 ml of methanol were distilled out of the reaction mixture and then the mixture was cooled again to room temperature. The reaction solution was adjusted to pH 2 with 410 ml of 37% aqueous hydrochloric acid, which precipitated the product out of the solution. The product suspension was stirred at room temperature for another 2 h, filtered off, and the filter residue was dried overnight at 40° C. under reduced pressure. 212.2 g (content: 92.4%, 83.8% of theory) of the pure Z product were obtained as a yellowish solid.

$^1$H NMR (400 MHz, $d_6$-DMSO): δ=3.67 (s, 3H, O—CH$_3$); 6.79 (d, 2H, Ar—H); 6.85 (s, 1H, Ar—CH=); 7.61 (d, 2H, Ar—H); 9.82 (bs, 1H, Ar—OH); 12.67 (bs, 1H, COOH).

$^{13}$C NMR (75 MHz, $d_4$-MeOH): δ=59.3 (O—CH$_3$); 116.5 ($C_{Ar}$—H); 125.8 (Ar—CH=); 126.2 ($C_{Ar}$—R); 133.1 ($C_{Ar}$—H); 144.8 (=C—OMe); 159.8 ($C_{Ar}$—OH); 168.1 (COOH).

Example 2

Preparation of (S)-3-(4-hydroxyphenyl)-2-methoxypropionic Acid Sodium Salt by Hydrogenation with Ruthenium Catalyst

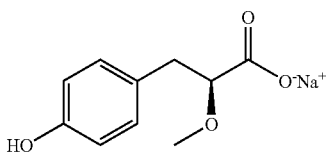

62:5 mg (1.0 mmol) of [RuCl$_2$(p-cymene)]$_2$ and 139.6 mg (2.1 mmol) of 2,2'-dichloro-3,3'-dimethoxy-6,6'-bisdiphenylphosphinyl)biphenyl were suspended in 150 ml of degassed methanol and heated under reflux for 1 h. The resulting solution was cooled to room temperature and added to a solution of 40.46 g (200 mmol) of Z-4'-hydroxy-2-methoxycinnamic acid in 150 ml of degassed methanol. Subsequently, the mixture was transferred into an autoclave and hydrogenated at 70° C. and 85 bar of hydrogen pressure for 16 h. The mixture was cooled, decompressed and freed of solvent under reduced pressure. The residue was taken up with 650 ml of isopropyl acetate, washed with 200 ml of 1N HCl and with 100 ml of saturated NaCl solution, concentrated to a volume of 500 ml and admixed with a solution of 19.7 g of sodium acetate in 163 ml of methanol. After approx. 1 h, the crystallization of the product began. After stirring for two hours, the product was filtered off with suction, washed with 40 ml of isopropyl acetate and dried at 40° C. under reduced pressure. 29.6 g (64% of theory, 92.7% ee) of the (S)-3-(4-hydroxyphenyl)-2-methoxypropionic acid sodium salt were obtained as a white crystalline solid.

Recrystallization from methanol/ethanol allowed the enantiomeric purity of the sodium salt to be additionally increased. To this end, 28 g of the sodium salt was suspended in 700 ml of ethanol and 350 ml of methanol, and 700 ml of solvent were distilled out of the suspension. Subsequently, the mixture was cooled to room temperature, filtered and dried under reduced pressure. 24 g of the sodium salt were obtained as a white crystalline solid (87% of theory, 97.4% ee).

$^1$H NMR (400 MHz, $D_2$O): δ=2.83 (dd, 1H, CH$_2$); 2.96 (dd, 1H, CH$_2$); 3.27 (s, 3H, O—CH$_3$); 3.87 (dd, 1H, O—CH); 6.85 (dt, 2H, Ar—H); 7.18 (dt, 2H, Ar—H).

Example 3

Preparation of (S)-3-(4-hydroxyphenyl)-2-methoxypropionic Acid Sodium Salt by Hydrogenation with Rhodium Catalyst

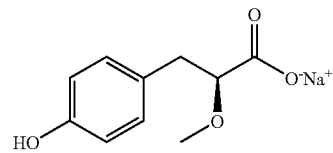

6.3 mg (0.0154 mmol) of Rh(COD)$_2$BF$_4$ and 6.8 mg (0.0154 mmol) of (S,S)-2,4-bis-(diphenylphosphinyl)pentane were dissolved in 1 ml of degassed methanol and added to a solution of 100 mg (0.51 mmol) of Z-4'-hydroxy-2-methoxycinnamic acid in 3 ml of degassed methanol. Subsequently, the mixture was transferred into an autoclave and hydrogenated at 50° C. and 3 bar of hydrogen pressure for 16 h. The mixture was cooled to room temperature, decompressed and freed of solvent under reduced pressure. The (S)-3-(4-hydroxyphenyl)-2-methoxypropionic acid was obtained as an oil with an enantiomeric excess of 80% (100% conversion of the substrate).

Example 4

Preparation of (S)-3-(4-hydroxyphenyl)-2-methoxypropionic Acid Sodium Salt by Hydrogenation with Iridium Catalyst

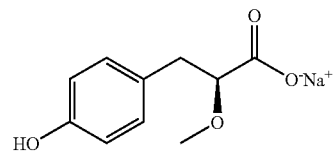

339 mg (0.5 mmol) of [Ir(COD)Cl]$_2$ and 445 mg (1.0 mmol) of (S,S)-2,4-bis(diphenylphosphinyl)pentane were dissolved in 80 ml of degassed methanol and added to a degassed solution of 40.16 g (200.0 mmol) of Z-4'-hydroxy- 2-methoxycinnamic acid in 240 ml of isopropyl acetate and 60 ml of methanol. Subsequently, the mixture was transferred to an autoclave and hydrogenated at 65° C. and 3 bar of hydrogen pressure for 24 h. The mixture was cooled to room temperature, decompressed and freed of solvent under reduced pressure. The residue was taken up in 400 ml of isopropyl acetate and admixed with a solution of 16.2 g (200 mmol) of sodium acetate in 143 ml of methanol. After approx. 1 h, the crystallization of the product began. After stirring for two hours, the product was filtered off with suction, washed with isopropyl acetate and then dried at 40° C. under reduced pressure. 25.6 g (53% of theory, 92% ee) of the (S)-3-(4-hydroxyphenyl)-2-methoxypropionic acid sodium salt were obtained as a white crystalline solid. Recrystallization from methanol/ethanol allowed the enantiomeric purity of the sodium salt to be increased. To this end, 25 g of the sodium salt was suspended in 600 ml of ethanol and 300 ml of methanol, and 600 ml of solvent were distilled out of the suspension. Subsequently, the mixture was cooled to room temperature, filtered and dried under reduced pressure. 19 g of the sodium salt were obtained as a white crystalline solid (80% of theory, 97.9% ee).

TABLE 1

Summary of the results from Examples 2 to 4

| Transition metal compound | [RuCl$_2$(p-cymene)]$_2$ | Rh(COD)$_2$BF$_4$ | Ir(COD)Cl]$_2$ |
|---|---|---|---|
| Ligand | (+)-ClMeOBiPHEP | (S,S)-BDPP | (S,S)-BDPP |
| Substrate/catalyst ratio | 1000 | 100 | 200 |
| Solvent | Methanol | Methanol | Isopropyl acetate/methanol |
| Additive | Triethylamine 1 eq | — | — |
| Temperature | 70° C. | 50° C. | 65° C. |
| H$_2$ pressure | 85 bar | 3 bar | 3 bar |
| Reaction time | 16 h | 24 h | 24 h |
| ee (in solution) | 78% | 80% | 90% |
| ee (after 1st crystallization) | 92% | Not determined | 92% |
| ee (after 2nd crystallization) | 97% | — | 97% |
| Yield | 56% | Not determined | 43% |

The invention claimed is:

1. Process for preparing enantiomerically enriched compounds of the general formula (I)

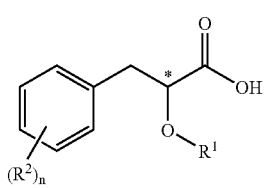

(I)

where
R$^1$ is an optionally substituted C$_1$-C$_{18}$-alkyl radical, an optionally substituted C$_4$-C$_{24}$-aryl radical or an optionally substituted C$_5$-C$_{18}$-arylalkyl radical,
R$^2$ are each independently OH, halogen, pseudohalogen, amino, an optionally substituted C$_1$-C$_{18}$-alkyl radical, an optionally substituted C$_1$-C$_{18}$-alkoxy radical, an optionally substituted C$_4$-C$_{24}$-aryl radical, an optionally substituted C$_5$-C$_{18}$-arylalkyl radical, an optionally substituted C$_1$-C$_{18}$-alkylsulphonyl radical, an optionally substituted C$_1$-C$_{18}$-alkylcarboxyl radical, an optionally substituted C$_1$-C$_{18}$-alkylcarbonyl radical, an optionally substituted C$_1$-C$_{18}$-mono- or dialkylamino radical, an optionally substituted C$_1$-C$_{18}$-alkylsulphonylamino radical or an optionally substituted C$_1$-C$_{18}$-acylamino radical, and
n is 0 or an integer from 1 to 5, characterized in that compounds of the general formula (II)

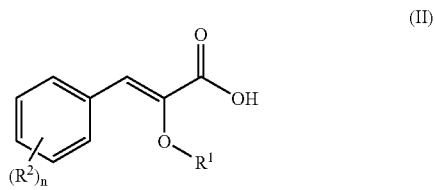

(II)

where
R$^1$, R$^2$ and n are each as defined for the general formula (I) are hydrogenated enantioselectively in a solvent and in the presence of a transition metal hydrogenation catalyst system comprising at least one transition metal compound and at least one ligand, wherein the transition metal compound(s) and ligand(s) are soluble in the solvent, and wherein the ligand is selected from the group consisting of (−)-2,2'-dichloro-3,3'-dimethoxy-6,6'-bis(diphenylphosphinyl)biphenyl, (−)-3,3'-bis(diphenylphosphinyl)-[4,4']bi(dibenzofuranyl), and the particular enantiomer.

2. Process according to claim 1, wherein the compounds of the general formula (II) are prepared from compounds of the general formula (III)

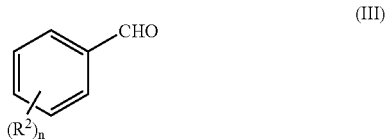

(III)

where
R$^2$ and n are each as defined in claim 1, and compounds of the general formula (IV)

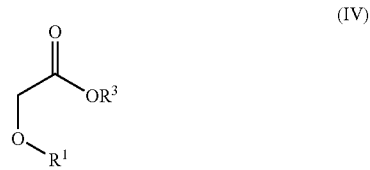

(IV)

where
R$^3$ is H or an optionally substituted C$_1$-C$_{18}$-alkyl radical, preferably a C$_1$-C$_6$-alkyl radical, and R$^1$ is as defined in claim 1 in an aldol reaction in the presence of a base, and subsequent hydrolysis if appropriate.

3. Process according to claim 1, wherein R$^1$ is an optionally substituted C$_1$-C$_6$-alkyl radical, preferably methyl.

4. Process according to claim 1, wherein R$^2$ is independently OH, F, Cl, Br, CN, an optionally substituted C$_1$-C$_6$- alkyl radical, an optionally substituted $C_6$-$C_{24}$-aryl radical or an optionally substituted $C_5$-$C_{18}$-arylalkyl radical, preferably OH.

5. Process according to claim 1, wherein n is 1, 2 or 3, preferably 1.

6. Process according to claim 1, wherein the transition metal hydrogenation catalyst system comprises at least one ruthenium, rhodium, or iridium compound and at least one ligand.

7. Process according to claim 1, wherein the transition metal hydrogenation catalyst systems comprises ruthenium, rhodium or iridium compounds of the Ru(II), Rh(I), Ir(I) oxidation states, in each case in combination with a chiral diphosphine ligand.

8. Process according to claim 1, wherein the ruthenium, rhodium or iridium compound used is [RuCl$_2$(p-cymene)]$_2$, Ru(COD)Cl$_2$, [Ru(C$_6$H$_6$)Cl$_2$]$_2$, Rh(COD)$_2$BF$_4$, [Rh(COD)Cl]$_2$, Rh(NBD)$_2$BF$_4$, [Rh(NBD)Cl]$_2$, Ir(COD)$_2$BF$_4$ or [Ir(COD)Cl]$_2$.

9. Process according to claim 1, wherein the enantioselective hydrogenation is performed in the presence of at least one protic solvent.

10. Process according to claim 9, wherein the solvents used are selected from the group consisting of alcohols, carboxylic esters, halogenated aliphatic hydrocarbons, cyclic or aliphatic ethers, cyclic or aliphatic hydrocarbons, aromatic hydrocarbons, or or mixtures thereof or comprising one or more thereof.

11. Process according to claim 1, wherein the enantioselective hydrogenation is performed at temperatures of 10° C. to 120° C.

12. Process according to claim 1, wherein the enantioselective hydrogenation is performed at 1 to 200 bar of hydrogen pressure.

13. Process according to claim 2, wherein the base used in the aldol reaction comprises alkali metal or alkaline earth metal $C_1$-$C_{18}$-alkoxides or optionally substituted alkali metal or alkaline earth metal $C_1$-$C_{18}$-amides.

14. Process according to claim 2, wherein the aldol reaction is performed in the presence of at least one solvent.

15. Process according to claim 14, wherein the solvents used are selected from the group consisting of alcohols, cyclic or open-chain ethers, aromatic hydrocarbons, cyclic or aliphatic hydrocarbons, or mixtures thereof or comprising one or more thereof.

16. Process according to claim 2, wherein the aldol reaction is performed at temperatures of 10° C. to 120° C.

17. Process according to claim 1, wherein the compounds of the general formula (I) are crystallized out without intermediate isolation in the presence of an alkali metal or ammonium salt directly as salts of the general formula (V)

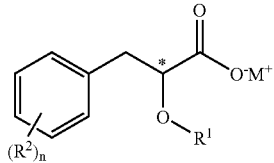

where
M$^+$ is an alkali metal cation or ammonium, preferably Na$^+$, and
R$^1$, R$^2$ and n are each as defined in claim 1.

18. Process according to claim 1, wherein the at least one transition metal compound is at least one iridium compound.

* * * * *